United States Patent
Loda

(10) Patent No.: US 6,690,020 B2
(45) Date of Patent: Feb. 10, 2004

(54) COMPACT SELF-SHIELDED IRRADIATION SYSTEM AND METHOD

(75) Inventor: Gary K. Loda, Pleasanton, CA (US)

(73) Assignee: Surebeam Corporation, San Diego, CA (US)

(*) Notice: Subject to any disclaimer, the term of this patent is extended or adjusted under 35 U.S.C. 154(b) by 0 days.

(21) Appl. No.: 09/971,986

(22) Filed: Oct. 4, 2001

(65) Prior Publication Data

US 2003/0066970 A1 Apr. 10, 2003

(51) Int. Cl.$^7$ ................................................. G21K 5/10
(52) U.S. Cl. ..................................... 250/455.11; 378/64
(58) Field of Search ......................... 250/455.11, 492.2, 250/492 R, 453.11; 378/64

(56) References Cited

U.S. PATENT DOCUMENTS

| | | | |
|---|---|---|---|
| 3,506,825 A | 4/1970 | Hartmann | |
| 4,484,341 A | 11/1984 | Luniewski | |
| 5,608,224 A | 3/1997 | Alvord | |
| 5,792,421 A | * 8/1998 | Riley | 422/21 |
| 6,177,677 B1 | 1/2001 | Alboresi et al. | |
| 6,504,898 B1 | * 1/2003 | Kotler et al. | 378/64 |

FOREIGN PATENT DOCUMENTS

| | | |
|---|---|---|
| WO | PCT/WO01/00249 A1 | 1/2001 |
| WO | PCT/WO01/25754 A1 | 4/2001 |

* cited by examiner

Primary Examiner—John R. Lee
Assistant Examiner—Phillip A Johnson
(74) Attorney, Agent, or Firm—Fulwider Patton

(57) ABSTRACT

An accelerator provides radiant energy in a first direction A carousel and first and second members have a common axis in the first direction. The carousel, preferably cylindrical, has a ring-shaped configuration defined by inner and outer diameters. The first member has an outer diameter preferably contiguous to the carousel inner diameter. The second member has an inner diameter preferably contiguous to the carousel outer diameter. The first and second members provide shielding against the radiant energy from the accelerator. A single motor (e.g., stepping motor) rotates the carousel past the radiant energy continuously at a substantially constant speed in successive revolutions. Vanes made from a shielding material are disposed at spaced positions in the carousel to divide the carousel into compartments for receiving the articles and to isolate each compartment from the radiant energy in other compartments. A loader loads the articles into compartments before the movement of the articles in the compartments past the radiant energy. An unloader unloads the articles from the compartments after the movement of the articles in the compartments past the radiant energy. The resultant system is simplified, is manufactured at a minimal cost and is operative in a minimal space for irradiating products without any significant sacrifice in the quality of the irradiation. It is especially utilized by companies of small or medium size where the irradiation of products is only sporadic.

44 Claims, 3 Drawing Sheets

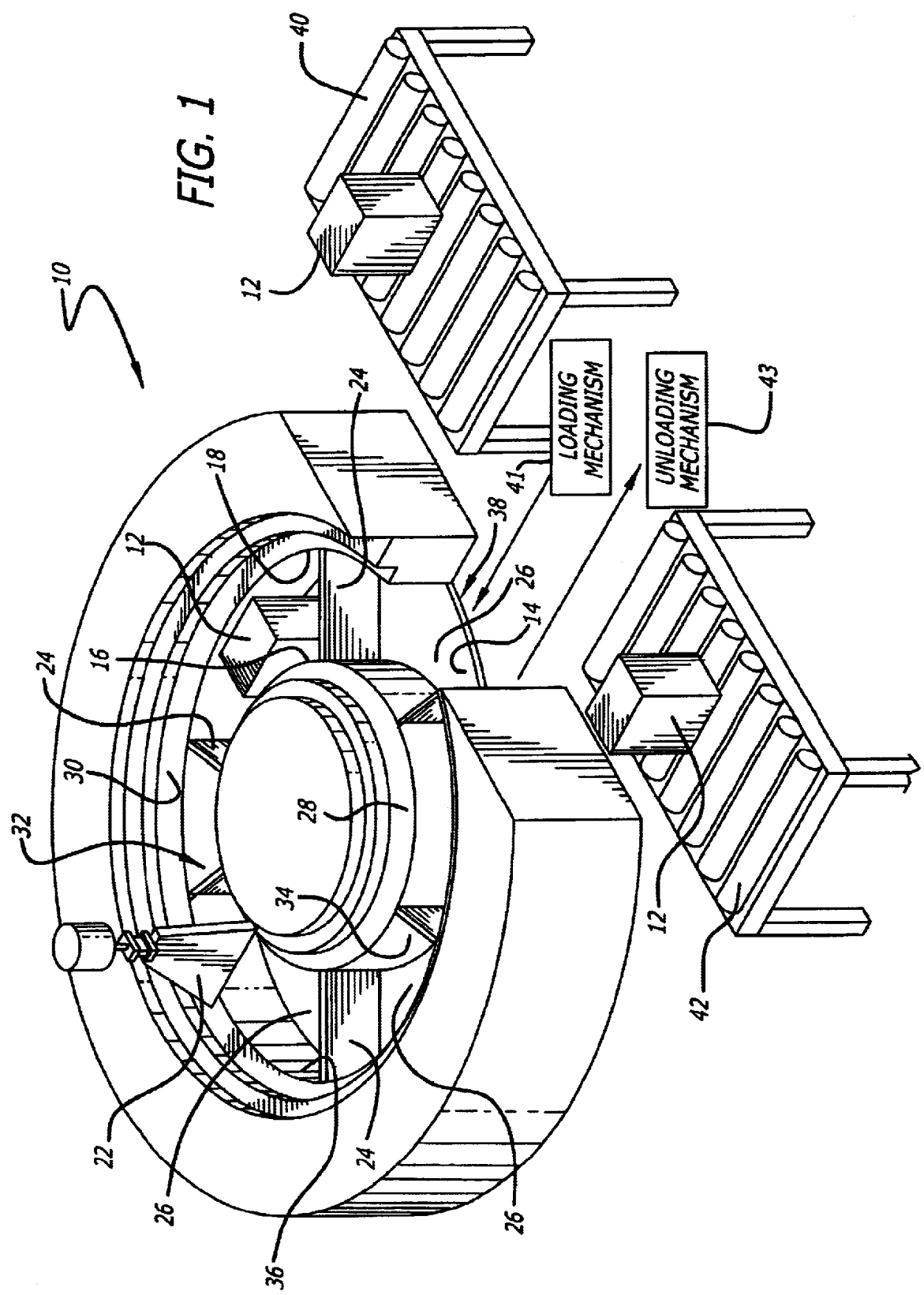

1

COMPACT SELF-SHIELDED IRRADIATION SYSTEM AND METHOD

This invention relates to systems for, and methods of, irradiating products, including food products to make them safe to use or eat. More particularly, the invention relates to systems for, and methods of, providing a simplified system in a minimal space and at a minimal cost without any significant sacrifice in the quality of the irradiation provided to the products including food products.

BACKGROUND OF A PREFERRED EMBODIMENT OF THE INVENTION

It has been known for some time that drugs and medical instruments and implements have to be irradiated so that they will not cause patients to become ill from harmful bacteria when they are applied to the patients. Systems have accordingly been provided for irradiating drugs and medical instruments and implements. The drugs and the medical instruments and implements have then been stored in sterilized packages until they have been ready to be used.

In recent years, it has been discovered that foods can carry harmful bacteria if they are not processed properly or, even if they are processed properly, that the foods can harbor and foster the proliferation of such harmful bacteria if they are not stored properly or retained under proper environmental conditions such as temperature. Some of the harmful bacteria can even be deadly.

For example, harmful bacteria have been discovered in recent years in hamburgers prepared by one of the large hamburger chains. Such harmful bacteria have caused a number of purchasers of hamburgers at stores in the chain to become sick. As a result of this incident and several other similar incidents, it is now recommended that hamburgers should be cooked to a well done, or at least a medium, state rather than a medium rare or rare state. Similarly, harmful bacteria have been found to exist in many chickens that are sold to the public. As a result of a number of incidents which have recently occurred, it is now recommended that all chickens should be cooked until no blood is visible in the cooked chickens.

To prevent incidents such as discussed in the previous paragraphs from occurring, various industries have now started to irradiate foods before the goods are sold to the public. This is true, for example, of hamburgers and chickens. It is also true of fruits, particularly fruits which are imported into the United States from foreign countries.

In previous years, gamma rays have generally been the preferred medium for irradiating various articles. The gamma rays have been obtained from a suitable material such as cobalt and have been directed to the articles to be irradiated. The use of gamma rays has had certain disadvantages. One disadvantage is that irradiation by gamma rays is slow. Another disadvantage is that irradiation by gamma rays is not precise. This results in part from the fact that the strength of the source (e.g. cobalt) of the gamma rays decreases over a period of time and that the gamma rays cannot be directed in a sharp beam to the articles to be irradiated. This prevents all of the gamma rays from being useful in irradiating the articles.

In recent years, electron beams have been directed to articles to irradiate the articles. Electron beams have certain advantages over the use of gamma rays to irradiate articles. One advantage is that irradiation by electron beams is fast. For example, a hamburger patty having a square cross section can be instantaneously irradiated by a passage of an electron beam of a particular intensity through the hamburger patty. Another advantage is that irradiation by an electron beam is relatively precise because the strength of the electron beam remains substantially constant even when the electron beam continues to be generated over a long period of time.

X-rays have also been used to irradiate articles. The x-rays may be formed from electron beams. An advantage in irradiating articles with x-rays is that the articles can be relatively thick. For example, x-rays can irradiate articles which are thicker than the articles which are irradiated by electron beams.

The systems now in use are relatively complicated and relatively expensive and occupy a considerable amount of space. These systems are particularly effective when used at companies requiring radiation of large volumes of products at a particular location. These companies are generally large and have considerable assets. No system apparently exists for irradiating reduced volumes of products at a particular location. No system apparently exists for use by companies of small or medium size.

BRIEF DESCRIPTION OF A PREFERRED EMBODIMENT OF THE INVENTION

This invention relates to a system for, and method of, providing a simplified system operative in a minimal space, and having a minimal cost, for irradiating products without any significant sacrifice in the quality of the radiation of products compared to the irradiation provided in the prior art. The invention is particularly effective for use by companies of small or medium size or where the irradiation of products is only sporadic.

An accelerator provides radiant energy in a first direction A carousel and first and second members have a common axis in the first direction. The carousel, preferably cylindrical, has a ring-shaped configuration defined by inner and outer diameters. The first member has an outer diameter preferably contiguous to the inner diameter of the carousel. The second member has an inner diameter preferably contiguous to the outer diameter of the carousel. The first and second members provide shielding against the radiant energy from the accelerator.

A single motor (e.g., stepping motor) rotates the carousel past the radiant energy continuously at a substantially constant speed in successive revolutions. Vanes made from a shielding material are disposed at spaced positions in the carousel to divide the carousels into compartments for receiving the articles and to isolate each compartment against the radiant energy in other compartments.

A loader loads the articles into compartments before the movement of the articles in the compartments past the radiant energy. An unloader unloads the articles from the compartments after the movement of the articles in the compartments past the radiant energy.

BRIEF DESCRIPTION OF THE DRAWINGS

In the drawings:

FIG. 1 is a perspective view of a preferred embodiment of the invention for irradiating articles, the preferred embodiment including a rotary carousel, compartments in the carousel and articles in the compartments;

DETAILED DESCRIPTION OF A PREFERRED EMBODIMENT OF THE INVENTION

Figure 3:
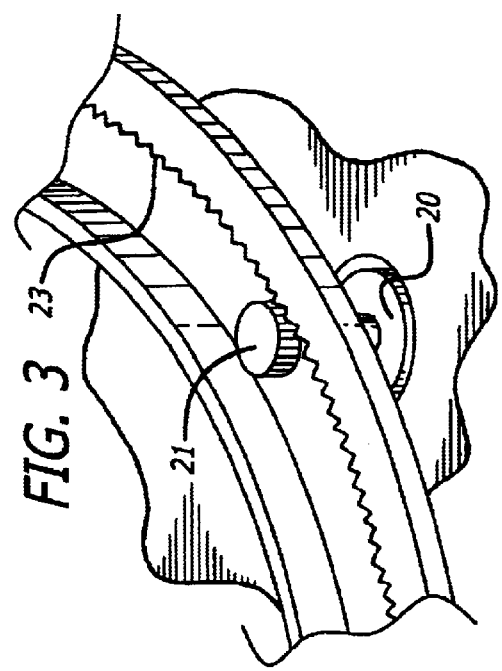
FIG. 3 is a fragmentary perspective view of the carousel and of a stepping motor arrangement for rotating the carousel at a substantially constant speed.
Figure 2:
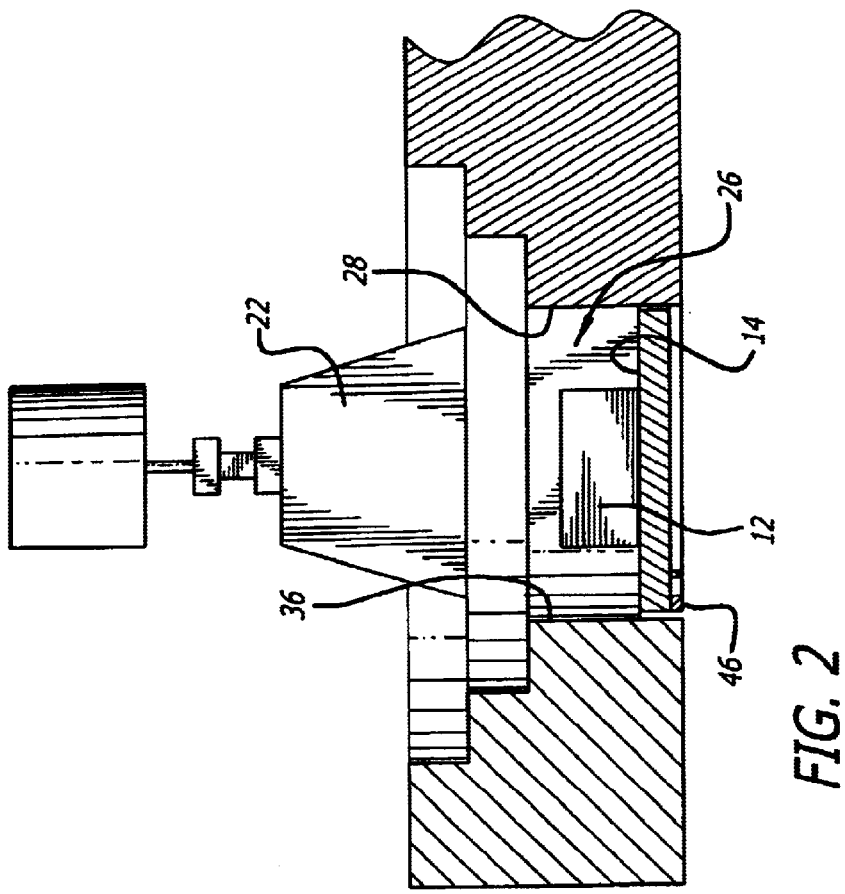
FIG. 2 is a fragmentary sectional view of the carousel, the compartments and the articles and of an accelerator for irradiating the articles in the compartments.
Figure 4:
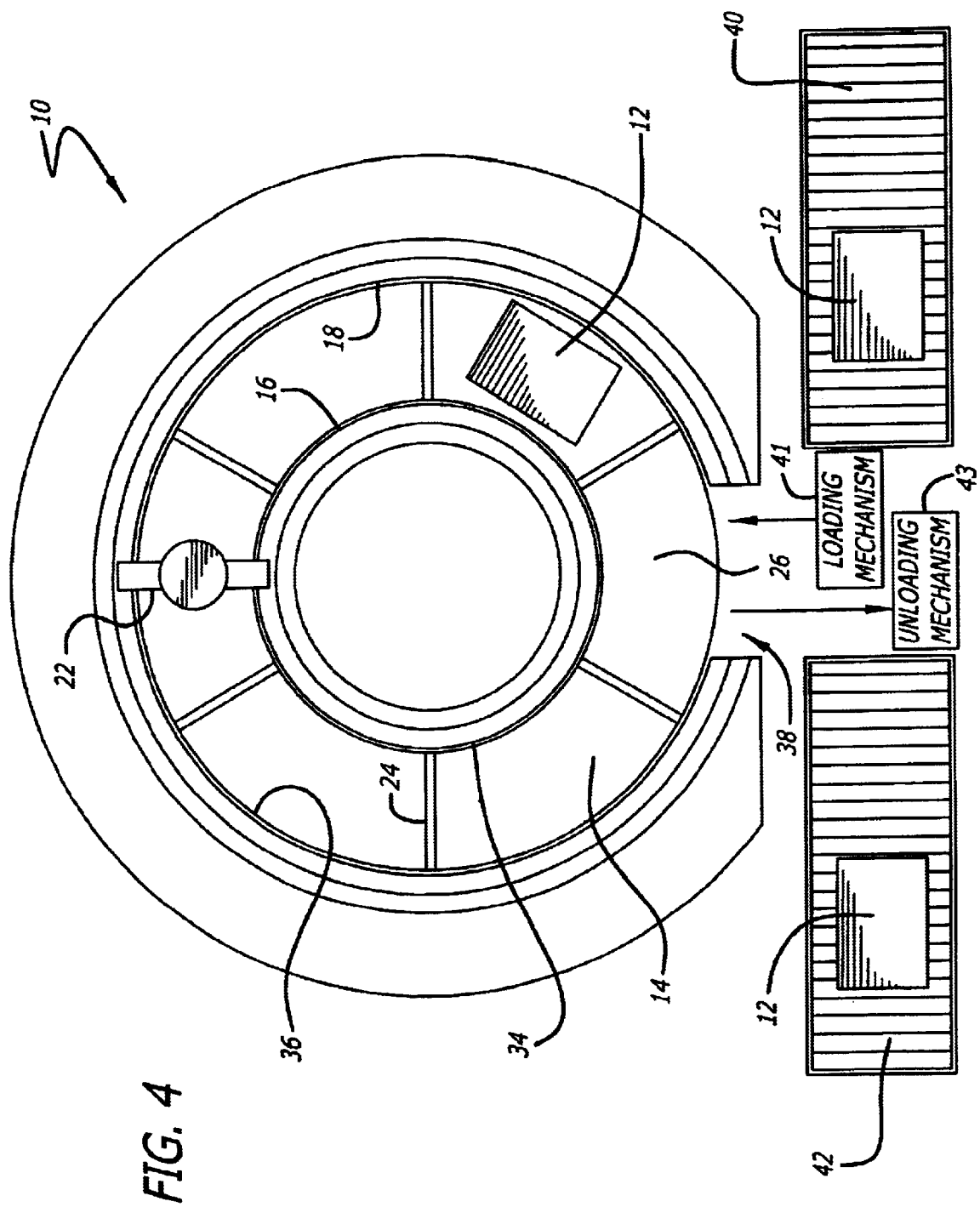
FIG. 4 is a top plan view of the preferred embodiment of the invention for irradiating articles.

A system generally indicated at 10 is provided for irradiating articles 12. The radiation may be provided by gamma rays, electron beams or x-rays, although electron beams are generally preferred. The articles 12 may be drugs, medical instruments and medical products which are irradiated so that they will not cause patients to become ill from harmful bacteria when they are applied to the patients. The articles 12 may also be different food articles such as meat, poultry, vegetables and fruit, particularly those imported from foreign countries.

The system 10 includes a carousel 14. The carousel 14 has a ring shape, preferably cylindrical, defined by an axis of rotation and by an inner diameter 16 and an outer diameter 18. The inner and outer diameter 16 and 18 of the carousel 14 are coaxial with the carousel axis of rotation. The carousel is rotatable as by a motor 20, preferably at a substantially constant speed. The motor 20 may be a stepping motor which drives a pinion gear 21 along a rack gear 23 provided in the carousel 14. The rotary movement of the carousel 14 is past radiation from a source or accelerator 22. The radiation from the source or accelerator 22 is in a direction corresponding to the axis to the axis of rotation of the carousel 14.

Vanes 24 are disposed in the carousel 14, preferably at spaced intervals in the annular direction around the carousel. The vanes 24 divide the carousel 14 into compartments 26 for receiving the articles 12. The vanes 24 may be made from suitable material such as a steel or other metal having properties of providing radiation shielding to prevent radiation in one compartment from entering into other compartments. The vanes 24 extend within the carousel 14 between the inner diameter 16 and the outer diameter 18 of the carousel. The vanes 20 particularly provide shielding in each compartment 26 against x-rays.

A radiation shielding member 28 is disposed within the inner diameter 16 of the carousel 14. The shielding member 28 is stationary and preferably cylindrical and is provided with the same axis as the carousel 14. The radiation shielding member 28 is preferably made from a suitable material such as concrete.

A radiation shielding member 30 is provided with a hole 32, preferably cylindrical and preferably having an axis corresponding to the axis of rotation of the carousel 14. Preferably the shielding member 30 is contiguous to the outer diameter 18 of the carousel 14. The shielding member 30 may be made from a suitable material such as steel or any suitable metal or from concrete or from a combination of steel and concrete.

Walls 34 and 36 define an opening 38 in the shielding member 30. Preferably the walls 34 and 36 are separated from each other to provide the opening 38 with an angle of approximately 45 degrees. A loading area 40 is provided adjacent the wall 36 to provide for the loading of the articles 12 on the carousel 14. Mechanisms 41 well known in the art may be provided for loading the articles 12 into the compartments 26 from the loading area 40. An unloading area 42 is provided adjacent the wall 36 to provide for the unloading of the articles 12 from the carousel 14 after the articles have been irradiated by the source or accelerator 22. Mechanisms 43 well known in the art may be provided for unloading the articles 12 from the compartments 26 into the unloading area 42.

The articles 12 are loaded into the compartments 26 at the loading area 40 while the carousel 14 is moved at a substantially constant speed by the stepping motor 20. The articles 12 then move at the substantially constant speed past the radiation from the source or accelerator 22. This causes progressive positions in the articles 12 to be irradiated with a substantially constant dosage of radiation. After being irradiated, the articles 12 move at the substantially constant speed to the unloading area 42 where the articles are unloaded from the carousel 14.

The articles 12 may have irregular shapes. This causes the radiation dosage at progressive positions in the articles 12 to vary dependent upon the thickness of the articles at these positions. Application Ser. No. 09/912,576 (Attorneys file 57333) discloses a system for providing fixtures complementary to the irregular configuration of the articles at the progressive position. These fixtures cause the radiation dosage of the articles at progressive positions in the articles to be substantially constant, within acceptable limits, even with irregularities in the configuration of the articles at the progressive positions.

The system 10 disclosed above irradiates the articles 12 from only one side of the articles. If it is desired to irradiate the articles 12 from two (2) opposite sides of the articles, the articles may be rotated through an angle of 180 degrees to expose the second side of the articles to radiation from the source or accelerator 22. Alternatively, a second source or accelerator may be disposed on the opposite side of the articles from the source or accelerator 22 to irradiate the second side of the articles. These arrangements are well known in the art.

The system and method described above have certain important advantages over the prior art. For example, the manufacturing cost and the floor space required by the system is considerably less than is presently being provided. This difference may be by as much as a factor of four (4). Furthermore, the system and method of this invention extend the market to customers who cannot afford the system now being furnished and offered in the market. Novel and patentable features of this invention include the closed loop ring-shaped carousel, the single motor for driving the carousel at a substantially constant speed, the radiation shielding within the carousel and outside of the carousel and the vanes for dividing the carousel into compartments and for shielding the articles in the compartments against extraneous radiation, particularly x-rays.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

What is claimed is:

1. In combination for applying radiant energy to articles,
an accelerator for providing the radiant energy in a first direction,
a ring-shaped carousel for rotating the articles past the radiant energy from the accelerator on an axis corresponding to the first direction,
a loading mechanism for disposing the articles in the carousel for a rotary movement of the articles with the carousel past the radiant energy from the accelerator,
an unloading mechanism for removing the articles from the carousel after the movement of the articles with the carousel past the radiant energy from the accelerator,
the carousel having an annular opening at the center of the carousel, and a member disposed in the annular opening for providing a shielding against the radiant energy.

2. In a combination as set forth in claim 1,
vanes disposed in the carousel at spaced intervals around the carousel for dividing the carousel into compartments for receiving the articles.

3. In combination for applying radiant energy to articles,
an accelerator for providing the radiant energy in a first direction,
a ring-shaped carousel for rotating the articles past the radiant energy from the accelerator on an axis corresponding to the first direction, a loading mechanism for disposing the articles in the carousel for a rotary movement of the articles with the carousel past the radiant energy from the accelerator, an unloading mechanism for removing the articles from the carousel after the movement of the articles with the carousel past the radiant energy from the accelerator, the carousel having an annular opening at the center of the carousel, and material disposed in the annular opening for providing a shielding against the radiant energy.

4. In a combination as set forth in claim 3, vanes disposed in the carousel at spaced intervals around the carousel for dividing the carousel into compartments for receiving the articles, the vanes being made from a material providing a shielding in each compartment from radiant energy from adjacent compartments.

5. In a compartment as set forth in claim 1, material disposed exterior to the carousel for providing shielding against radiant energy from the carousel and from the accelerator.

6. In combination for applying radiant energy to articles, an accelerator for providing the radiant energy in a first direction, a carousel having a ring-shaped configuration with inner and outer dimensions and rotatable past the radiant energy from the accelerator on a particular axis extending in the first direction, first material having the particular axis and having an outer dimension substantially corresponding to the inner dimension of the carousel and having properties providing shielding against the radiant energy from the accelerator, and second material having the particular axis and having an inner dimension substantially conforming to the outer dimension of the carousel and having properties of providing shielding against the radiant energy from the accelerator.

7. In a combination as set forth in claim 6, the carousel having an annular configuration and the first material having an annular configuration and being disposed within the annular configuration of the carousel and the second material having an annular configuration and the carousel being disposed within the annular configuration of the second material.

8. In a combination as set forth in claim 7, a loading mechanism for disposing the articles in the carousel for a rotary movement of the articles with the carousel past the radiant energy from the carousel, and an unloading mechanism for removing the articles from the carousel after movement of the articles with the carousel past the radiation energy from the accelerator.

9. In a combination as set forth in claim 7 wherein the carousel is rotated at a substantially constant speed past the radiant energy from the accelerator and wherein the articles are disposed within the carousel for movement with the carousel at the substantially constant speed past the radiant energy from the accelerator.

10. In a combination as set forth in claim 9 wherein the carousel is compartmentalized to provide for the disposition of the articles in the compartments.

11. In combination for applying radiant energy to articles, a carousel having a hollow configuration and movable continuously in a closed loop at a substantially constant speed, the carousel defining compartments for holding the articles for movement with the carousel, an accelerator disposed relative to the carousel to provide radiant energy to the articles in the carousel during the movement of the carousel continuously in the closed loop, a first member disposed within the hollow configuration of the carousel and having the configuration of the closed loop and having properties of shielding against the radiant energy from the accelerator, and a second member disposed externally of the carousel and having the configuration of the closed loop and having properties of shielding against the radiant energy from the accelerator.

12. In a combination as set forth in claim 11, a motor for driving the carousel at a substantially constant speed in the closed loop.

13. In a combination as set forth in claim 11 wherein the carousel, the first member and the second member are disposed on a common axis.

14. In a combination as set forth in claim 11 wherein the carousel, the first member and the second member are disposed in a common plane.

15. In a combination as set forth in claim 12 wherein the carousel, the first member and the second member are disposed on a common axis and wherein the carousel, the first member and the second member are disposed in a common plane.

16. In a combination as set forth in claim 11, a loading area disposed in a closely spaced relationship to the carousel for providing for a transfer of articles to the carousel for introduction of the radiant energy to the articles without interrupting the movement of the carousel, and an unloading area disposed in a closely spaced relationship to the carousel for providing for a transfer of the articles from the carousel after the provision of the radiant energy to the articles without interrupting the movement of the carousel.

17. In a combination as set forth in claim 15, a loading area disposed in a closely spaced relationship to the carousel for providing for a transfer of articles to the carousel for introduction of the radiant energy to the article without interrupting the movement of the carousel, and an unloading area disposed in a closely spaced relationship to the carousel for providing for a transfer of the articles from the carousel after the provision of the radiant energy to the articles without interrupting the movement of the carousel.

18. In combination for applying radiant energy to articles, an accelerator for providing radiant energy in a particular direction, a carousel rotatable past the radiant energy from the accelerator, a plurality of vanes disposed at spaced positions in the carousel to divide the carousel into compartments for receiving the articles, the vanes being made from a material providing a shielding against the radiant energy from the accelerator, the vanes being constructed and disposed in the compartments to shield the articles in each compartment from radiation from other compartments;

a loading mechanism for loading the articles into the compartments before the movement of the compartments past the radiant energy, and an unloading mechanism for unloading the articles from the compartments after the movement of the compartments past the radiant energy from the accelerator.

19. In a combination as set forth in claim 18 wherein the articles are movable continuously at a substantially constant speed from the loading mechanism past the radiant energy from the accelerator and then to the unloading mechanism.

20. In a combination as set forth in claim 19 wherein a single motor rotates the articles continuously at the substantially constant speed from the loading mechanism past the radiant energy from the accelerator and then to the unloading mechanism.

21. In a combination as set forth in claim 20 wherein the single motor is a stepping motor.

22. In a combination as set forth in claim 18 wherein an accelerator provides the radiant energy in a particular direction and wherein
the carousel is cylindrical and has an axis of rotation in a direction corresponding to the particular direction.

23. In a combination as set forth in claim 18 wherein the carousel is ring-shaped and wherein
first material having a cylindrical configuration is disposed within the ring defined by the carousel and wherein
the first material has properties of providing shielding against the radiant energy from the accelerator and wherein
the first material is coaxial with the carousel.

24. In a combination as set forth in claim 23 wherein the carousel is disposed within a cylindrical opening in a second material and wherein
the second material has properties of providing shielding against the radiant energy from the accelerator and wherein
the opening in the second material is coaxial with the carousel.

25. In combination for applying radiant energy to articles,
a carousel disposed in a looped configuration in a particular plane and movable in a closed loop in the particular plane,
vanes disposed in the carousel at spaced positions around the loop defined by the carousel to define compartments for receiving the articles, the vanes being made from a material shielding the articles in the compartments from radiation in adjacent compartments, and
an accelerator for providing the radiant energy, the accelerator being disposed to provide the radiant energy in a direction substantially perpendicular to the plane of the carousel and the plane of movement of the carousel in the closed loop, and
a motor operatively coupled to the carousel for moving the carousel in the closed loop.

26. In a combination as set forth in claim 25,
the carousel having an annular ring-shaped configuration and the compartments in the carousel being formed to provide for a movement of the articles in the compartment with the movement of the carousel.

27. In a combination as set forth in claim 26 wherein first material is disposed within the ring-shaped configuration of the carousel and is provided with a configuration corresponding to the configuration of the carousel and is provided with properties of shielding against the radiant energy from the accelerator and wherein
second material is disposed outside of the ring-shaped configuration of the carousel and is provided with a configuration of the carousel and is provided with properties of shielding against the radiant energy from the accelerator.

28. In a combination as set forth in claim 25 wherein the motor moves the carousel continuously through successive revolutions in the closed loop.

29. In a combination as set forth in claim 28 wherein the motor moves the carousel continuously at a substantially constant speed through the successive revolutions in the closed loop.

30. In a combination as set forth in claim 29 wherein the motor is a single motor and wherein
the articles are loaded into the compartments at a loading area and wherein
the articles are unloaded from the compartments at an unloading area separated from the loading area.

31. In a combination asset forth in claim 30 wherein the single motor is a stepping motor.

32. A method of applying radiant energy to articles, including the steps of:
providing a ring-shaped carousel rotatable on a particular axis,
disposing an accelerator to provide the radiant energy in a direction corresponding to the particular axis,
disposing the articles in the carousel for rotation with the carousel,
rotating the carousel to move the articles in the carousel past the radiant energy from the accelerator, and
shielding the space within the ring-shaped carousel and the space outside of the ring-shaped carousel against radiation from the accelerator.

33. A method as set forth in claim 32 wherein the carousel is rotated continuously in successive revolutions past the radiant energy from the accelerator at a substantially constant speed.

34. A method as set forth in claim 33 wherein the carousel has a configuration of a ring defined by inner and outer contours and wherein
a first member having an outer contour corresponding to the inner contour of the carousel is disposed within the ring-shaped configuration of the carousel and is provided with properties of shielding against radiation and wherein
a second member having an inner contour corresponding to the outer contour of the carousel is disposed in enveloping relationship to the ring-shaped configuration of the carousel and is provided with properties of shielding against radiation.

35. A method as set forth in claim 32 wherein vanes are provided in the carousel at spaced positions around the annular periphery of the carousel to define compartments in the carousel for holding the articles and wherein
the vanes are made from a material providing shielding in each compartment against the radiant energy in other compartments.

36. A method as set forth in claim 32 wherein the articles are stationary in the carousel.

37. A method as set forth in claim 32 wherein vanes are provided in the carousel at spaced positions around the annular periphery of the carousel to define compartments in the carousel for holding the articles and wherein
the vanes are made from a material providing shielding in each compartment against the radiant energy from other compartments and wherein the articles are stationary in the carousel.

38. In combination for applying radiant energy to articles, including:

a ring-shaped carousel disposed in a closed loop defined by an inner diameter and an outer diameter greater than the inner diameter and movable in the closed loop, a motor for rotating the ring-shaped carousel in the closed loop, an accelerator for directing radiant energy against the articles in the carousel, a first member disposed within the ring-shaped carousel and having a diameter less than the inner diameter of the carousel and made from a material providing a shielding against the radiant energy from the accelerator, and a second member enveloping the ring-shaped carousel and having a diameter greater than the outer diameter of the carousel and providing a shielding against the radiant energy from the accelerator.

39. In a combination as set forth in claim 38 wherein the motor is a single motor which rotates the carousel continuously at a substantially constant speed.

40. In a combination as set forth in claim 39 wherein the motor is a stepping motor.

41. In a combination as set forth in claim 38 wherein the carousel is cylindrical with a particular axis and wherein the carousel is rotatable on the particular axis and wherein the first member is cylindrical and is disposed on the particular axis and wherein the configuration of the second member in enveloping relationship to the carousel is cylindrical and the axis of the cylindrical configuration of the second member is the particular axis.

42. In a combination as set forth in claim 28 wherein the vanes are disposed at spaced positions around the annular periphery of the carousel to provide compartments for the articles and wherein the vanes in each compartment is made from a material providing shielding against the radiant energy in other compartments.

43. in a combination as set forth in claim 38 wherein the second member is cut at the positions between the loader and the unloader.

44. In a combination as set forth in claim 38 wherein the first member is contiguous to the carousel around the carousel at the inner diameter of the carausel and wherein The second member is contiguous to the carousel around the carousel at the outer diameter of the carousel.

* * * * *